United States Patent
Myllyoja et al.

(10) Patent No.: US 10,968,397 B2
(45) Date of Patent: Apr. 6, 2021

(54) RENEWABLE HYDROCARBONS, METHOD FOR PRODUCING THE SAME AND USE THEREOF

(71) Applicant: NESTE OYJ, Espoo (FI)

(72) Inventors: Jukka Myllyoja, Vantaa (FI); Marina Lindblad, Helsinki (FI); Mats Käldström, Porvoo (FI); Rami Piilola, Helsinki (FI); Elias Ikonen, Espoo (FI)

(73) Assignee: NESTE OYJ, Espoo (FI)

( * ) Notice: Subject to any disclaimer, the term of this patent is extended or adjusted under 35 U.S.C. 154(b) by 0 days.

(21) Appl. No.: 15/392,886

(22) Filed: Dec. 28, 2016

(65) Prior Publication Data

US 2017/0183570 A1    Jun. 29, 2017

(30) Foreign Application Priority Data

Dec. 29, 2015 (EP) .................................... 15202932

(51) Int. Cl.
| | |
|---|---|
| *C10G 3/00* | (2006.01) |
| *C10G 45/00* | (2006.01) |
| *C07C 51/377* | (2006.01) |
| *C10G 45/08* | (2006.01) |
| *C10G 45/10* | (2006.01) |
| *C07C 51/00* | (2006.01) |

(52) U.S. Cl.
CPC .............. *C10G 3/46* (2013.01); *C07C 51/00* (2013.01); *C07C 51/377* (2013.01); *C10G 3/47* (2013.01); *C10G 3/50* (2013.01); *C10G 45/08* (2013.01); *C10G 45/10* (2013.01); *C10G 2300/1011* (2013.01); *C10G 2300/202* (2013.01); *C10G 2400/02* (2013.01); *Y02P 30/20* (2015.11)

(58) Field of Classification Search
CPC .............. C10G 3/42; C10G 3/47; C10G 3/50
USPC .................................................. 585/254, 733
See application file for complete search history.

(56) References Cited

U.S. PATENT DOCUMENTS

| | | |
|---|---|---|
| 8,003,818 B2 | 8/2011 | Van Den Brink et al. |
| 2006/0135793 A1* | 6/2006 | Blessing ............... C07C 51/377 549/318 |
| 2006/0162239 A1 | 7/2006 | Van Den Brink et al. |

(Continued)

FOREIGN PATENT DOCUMENTS

| | | |
|---|---|---|
| CN | 101087749 A | 12/2007 |
| EP | 2 924 097 A2 | 9/2015 |

(Continued)

OTHER PUBLICATIONS

Dictionary.com, "How to Use the Slash", Dictionary.com, accessed Dec. 3, 2020, pp. 1-2 (Year: 2020).*

(Continued)

*Primary Examiner* — Philip Y Louie
(74) *Attorney, Agent, or Firm* — Buchanan Ingersoll & Rooney PC (57) ABSTRACT

A method for conversion of levulinic acid and to a hydrocarbon composition obtainable by the method. The method includes a step of providing a feedstock, a conversion step of subjecting the feedstock to a C—C coupling reaction and a hydrotreatment, and a hydrodeoxygenation step. The content of levulinic acid dimer derivatives having 4 oxygen atoms subjected to the hydrodeoxygenation step is 20 wt.-% or more.

19 Claims, 6 Drawing Sheets

(56) References Cited

U.S. PATENT DOCUMENTS

2012/0283493 A1* 11/2012 Olson .................. C10L 1/08
585/242
2013/0217932 A1* 8/2013 Seck .................. C10G 3/50
585/251

FOREIGN PATENT DOCUMENTS

WO    WO 2006/067171 A    6/2006
WO    WO 2015/144994 A1    10/2015

OTHER PUBLICATIONS

Ultius.com, "Slash/Virgule", Ultius.com, accessed Dec. 3, 2020, pp. 1-2 (Year: 2020).*

Office Action dated Feb. 2, 2021, by Chinese Patent Office in corresponding Chinese Patent Application No. 201611248573.1. (9 pages) English Translation (Year: 2021).*

European Search Report dated May 30, 2016 for application No. 15202932.8.

Search Report and Written Opinion dated Jan. 22, 2020, by the Brazilian Patent Office in corresponding Brazilian Application No. BR102016030792-9. (4 pages).

First Office Action dated May 7, 2020, by the Chinese Patent Office in corresponding Chinese Patent Application No. 201611248573.1, and an English Translation of the Office Action. (23 pages).

Office Action dated Feb. 2, 2021, by the Chinese Patent Office in corresponding Chinese Patent Application No. 201611248573.1. (9 pages).

* cited by examiner

RENEWABLE HYDROCARBONS, METHOD FOR PRODUCING THE SAME AND USE THEREOF

TECHNICAL FIELD

The present invention relates to methods for catalytic conversion of levulinic acid, products obtainable by such methods, use of such products for the production of liquid hydrocarbons, fuel or chemicals. In particular, the present invention relates to the catalytic conversion of levulinic acid from renewable sources for the production of chemicals and/or fuel components.

BACKGROUND ART

Aldol condensation of levulinic acids producing C10 units is known from US 2012/0283493 A1. The reaction product of the aldol condensation is further subjected to a hydrodeoxygenation step.

Alternative measures for aldol condensation of levulinic acids to dimeric derivative levulinic acid products are disclosed in WO 2006/067171 A1 and US 2006/0135793 A1. In the Examples, WO 2006/067171 A1 discloses preparing a dimer derivative mixture comprising 4-methyl-6-oxononanedioic acid (having 5 oxygen atoms) and other dimer derivatives. The following dimer derivatives are specifically mentioned in WO 2006/067171 A1:

DISCLOSURE OF THE INVENTION

The present invention relates to catalytic conversion of levulinic acid, including methods for aldol condensation, hydrotreatment and control of the ratio of components formed through reaction routes using hydrogen pressure regulation over catalytic conversion, hydrotreatment and hydrodeoxygenation, products obtainable by such methods having decreased naphthene content, which improve end-product properties and can be used in the production of liquid hydrocarbons, gasoline, JET fuel or diesel fuel and/or chemicals.

In the prior art, upgrading of levulinic acids derived from renewable sources encountered the problem that the properties of the obtained products were undesirable due to a large amount of cyclic compounds (naphthenes), high-molecular weight components and/or due to broad product distribution. Accordingly, in order to use the prior art products as fuel components or chemicals, it was necessary to further convert the obtained products, leading to increased complexity of the production process and large amounts of low value (or waste) components.

While fractional distillation is a method which is well established in the field of petrochemistry, this technique is only suited to provide separation for unreactive components. Biobased conversion products are typically reactive at high temperatures even in distillation separations. Accordingly, undesired products having a boiling point within the range of the product fraction cannot be separated using this technique and usually remain in the final product, thus deteriorating the product properties. Similarly, high molecular components remaining after distillation are usually of low value as fuels and chemicals.

The present invention aims at providing a less complex process for upgrading levulinic acid while reducing the amount of undesired components in the final product.

This problem is solved by the methods as defined in the appended claims.

Further, the present invention provides the products obtained by these methods which can be used as fuel components and/or chemicals e.g. after fractional distillation without further purification due to their low content of undesired components (e.g. acids, phenols, higher amount of naphthenes etc.).

DETAILED DESCRIPTION OF THE INVENTION

The present invention relates to a method for conversion of levulinic acid (LA) comprising a conversion step of subjecting a feedstock to a C—C coupling reaction and hydrotreatment so as to produce a LA-dimer/oligomer derivative. At least the LA-dimer derivative(s) and preferably further the levulinic acid oligomer derivative(s) is/are subjected to a final hydrodeoxygenation (HDO) reaction in a HDO step. The content of levulinic acid dimer derivatives having 4 oxygen atoms is 20 wt.-% or more relative to all LA dimer derivatives fed to the final HDO reaction. Using this method, the cyclisation tendency during the final HDO reaction of LA-dimer/oligomer (derivative) is decreased and therefore paraffin/naphthene-ratio of product is higher.

The present invention further provides a method for conversion of levulinic acid comprising a step of providing a feedstock comprising levulinic acid, a conversion step of subjecting the feedstock to a C—C coupling reaction. The C—C coupling reaction is carried out using an acidic ion exchange resin as a catalyst in the presence of hydrogen. The ion exchange resin carries (or contains) a hydrogenating metal. As a result of the conversion step, a conversion product containing LA-dimer/oligomer derivative(s) is obtained. At least the LA-dimer derivative(s) and preferably further the levulinic acid oligomer derivative(s) contained in the conversion product is subjected to a final hydrodeoxygenation (HDO) reaction at a temperature of at least 280° C. to obtain a HDO product. In the present invention, the content of levulinic acid dimers/oligomers having 4 oxygen atoms is 20 wt.-% or more.

In the present invention, levulinic acid is employed in the feedstock.

The levulinic acid may be employed in acid form or as a derivative selected from the group of esters of the levulinic acid and/or lactones of the levulinic acid.

In the step of subjecting the feedstock to the C—C-coupling reaction, levulinic acid or its derivative undergoes a C—C-coupling reaction with another levulinic acid or its derivative present in the feedstock so as to produce a levulinic acid dimer/oligomer.

Depending on the actual reaction conditions, the levulinic acid or its derivative may undergo different C—C-coupling reactions. In particular, the C—C-coupling reactions may be ketonisation reactions or reactions proceeding through an enol or enolate intermediate. Accordingly, the C—C-coupling reactions may be aldol-type reactions and condensations, ketonisations, reactions where the C—C-coupling involves an alkene, as well as other dimerization reactions. Further, decarboxylation, dehydration and/or hydrogenation may occur during or after the C—C-coupling reaction, thus providing a dimer derivative having less oxygen and/or carbon atoms than expected from the C—C-coupling reaction only.

The levulinic acid dimer/oligomer derivative thus includes all compounds directly obtainable from the levulinic acid dimer/oligomer by other reactions such as lactonisation and dehydroxylation. Examples of levulinic acid dimers according to the invention obtained by aldol-reaction are shown by the following formulas:

Since these dimers are not very stable under the reaction conditions of the C—C-coupling reaction, these dimers undergo further reactions such as lactonisation, dehydration and partial hydrogenation. Examples of levulinic acid dimer derivatives according to the invention are shown by the following formulas examples:

Without wanting to be bound to theory, it is considered that the IER catalyst catalyses mainly aldol condensation reactions of levulinic acid. The resulting dimers easily undergo lactonisation in the further procedure.

By appropriately adjusting the C—C-coupling reaction conditions and/or subjecting the C—C-coupling product (condensation product) to a preliminary hydrogenation (or preliminary hydrodeoxygenation) reaction under mild conditions, the composition of the conversion product can be shifted towards levulinic acid dimer derivatives having no keto groups (and preferably no C=C double bonds) in the middle of the LA-dimer molecule (4 oxygen atom products). These derivatives show lower internal cyclisation reactivity as compared to the derivatives having 5 oxygen atoms (having a keto group in the middle of molecule in addition to e.g. carboxylic acid groups or ester groups), so that further internal C—C-coupling reactions under the high-temperature conditions of the final hydrodeoxygenation step can be suppressed to a certain degree. Accordingly, the resulting HDO product has lower amount of cyclic compounds. Furthermore, it has surprisingly been found that the HDO product contains less aromatics.

By employing levulinic acid in the feedstock, the products obtained by the present invention are particularly suited as gasoline, jet fuel and/or diesel fuel components after fractionation. Specifically, in this case, the method of the present invention mainly provides paraffinic hydrocarbons (having a high content of isoparaffins) having 8 to 15 carbon atoms, wherein the majority of the product has 9 or 10 carbon atoms.

In other words, it was confirmed that the present method in general provides mainly hydrocarbons which are obtained by hydrogenation (hydrodeoxygenation) of levulinic acid dimers/oligomers, while even the severe conditions of the final (full) HDO step lead only to a low degree of further cyclisation and/or oligomerization.

The calculated greenhouse gas (GHG) emissions of fuel and the reduction potential of GHG emissions (compared to fossil based fuels) is a very important factor, when new fuel candidates are evaluated. Bio feedstocks typically consist of molecules contain a large amount of oxygen. Oxygen in the molecules does not contribute to combustion and thus reduces the energy density. Therefore, the oxygen is usually removed from a product before being used as a fuel component. The removal of oxygen is very commonly done by hydrodeoxygenation (HDO), which requires hydrogen. Hydrogen, however, is typically produced from fossil based feedstocks, so that the extent of the GHG reduction of bio based product depends very much on the amount of hydrogen required during the production of the fuel component.

It was decided in the EU (EU directive 2009/28/EU, 23 Apr. 2009), that after the 1st of Jan. 2018 biofuels produced in new plants (production started after 1 Jan. 2017) should reduce greenhouse gases (GHG) by more than 60% (compared to fossil fuel).

The full HDO conversion of a levulinic acid dimer (unsaturated C10-keto diacid) to C10-paraffin requires rather much hydrogen and the theoretical GHG reduction value (based on preliminary calculations) might be lower than the required 60%. The formation of some cyclic components will reduce the GHG emission to some extent, but decreases the quality of especially diesel fuel. However during the HDO also some decarboxylation occurs. This reaction does not require hydrogen and removes oxygen in the form of $CO_2$. If one carboxylic group of a LA-dimer is removed as $CO_2$, LA-dimer can produce a C9-paraffin which provides a GHG reduction potential of about 65%. Additionally, if both carboxylic groups of an intermediate LA-dimer are removed by decarboxylation (as $CO_2$), a C8-paraffin is formed and the calculated GHG reduction potential improves to over 70%. Therefore, the deoxygenation reaction route is important for improving the calculated GHG reduction potentials. By controlling the deoxygenation reaction route, it is possible to control the GHG reduction potential, which is very important for bio based fuel.

If bio based hydrogen is used (which is not typical due to the high costs of bio based hydrogen at the moment), the GHG reduction potential is >90%.

The content of levulinic acid dimer derivatives having 4 oxygen atoms (in the conversion product) is 20 wt.-% or more. The content can be determined from GC-MS analysis using at least the above-identified levulinic acid dimers and dimer derivatives as a reference. The content (wt.-%) of levulinic acid dimer derivatives having 4 oxygen atoms corresponds to the area percentage in the GC-MS total ion chromatogram (TIC) which can be attributed to LA dimer derivatives having 4 oxygen atoms (4ox) relative to the area in the GC-MS TIC which can be attributed all LA dimer derivatives in the conversion product. In other words, the above mentioned area percentage acquired via integration of GC-electron ionization-MS TIC corresponds to the weight percentage, i.e. 30 A-%≈30 wt.-%. The content of levulinic acid dimer derivatives having 4 oxygen atoms in the conversion product (fed to the final HDO step) is preferably 25 wt.-% or more, more preferably 30 wt.-% or more, 35 wt.-% or more, 40 wt.-% or more, 45 wt.-% or more, or 50 wt.-% or more. Although not particularly limited, this content is suitably 90 wt.-% or less, 80 wt.-% or less, 70 wt.-% or less, or 65 wt.-% or less in view of most favourable product properties.

When adjusting the reaction conditions such that the content of levulinic acid dimer derivatives having 4 oxygen atoms in the conversion product is 20 wt.-% or more, oligomerization and internal cyclisation can be further reduced, thus leading to more favourable product distribution.

Lactones are formed by intramolecular reaction of the levulinic acid dimers. This reaction is promoted by high temperatures. It has been found by the present inventors that the formation of undesired side-products in the (final) hydrodeoxygenation step can be suppressed by reducing the amount of lactone-type levulinic acid dimers fed to the hydrogenation step. When keeping the amount of lactone-type dimers in the feed to the (final) hydrodeoxygenation step at below 40% by weight, the HDO product contains less cyclic and aromatic compounds while the octane and cetane number is increased, thus improving the suitability as gasoline and diesel fuel components. The content of lactone-type dimers is preferably less than 30% by weight, more preferably less than 25% by weight, relative to all levulinic acid dimer derivatives fed to the final HDO step.

The present inventors surprisingly found that the formation of lactones can be suppressed by conducting the C—C-coupling reaction at high hydrogen pressure of at least 20 bar (absolute) when employing an ion exchange resin (IER) carrying (or containing) a hydrogenating metal.

In the present invention, the HDO product preferably contains at least 5% by weight of hydrocarbons derived from levulinic acid oligomers (trimers and higher oligomers). The content of the hydrocarbons derived from levulinic acid oligomers in the HDO product can be determined by GC-MS in the same manner as the content of levulinic acid dimer derivatives having 4 oxygen atoms. The content of the hydrocarbons derived from levulinic acid oligomers in the HDO product is more preferably at least 6% by weight, at least 7% by weight or at least 8% by weight.

The method of the present invention can provide products having a high content (more than 50%) of paraffinic hydrocarbons derived from levulinic acid dimers, i.e. having 10-x carbon atoms, wherein x is a number in the range of 0 to 3, preferably 0 to 2, more preferably 0 or 1. However, a certain amount of higher molecular weight compounds (namely hydrocarbons derived from levulinic acid trimers and higher oligomers) is favourable in particular for fuel applications, since such a carbon number distribution mimics that of fossil oil fractions (fossil fuel).

The final hydrodeoxygenation (HDO) reaction (the reaction for fully removing oxygen; i.e. to a total content of less than 1.0 atom-%, preferably less than 0.5 atom-% or less than 0.1 atom-%) is preferably carried out at a temperature of at least 280° C., preferably at least 290° C., more preferably at least 300° C., at least 305° C., or at least 310° C.

The present inventors found that a temperature of 280° C. or more in the final HDO step using a conventional feed leads to further (thermal) C—C-coupling reactions (further cyclisation, aromatisation, phenol formation and oligomerization reactions) in the HDO step. Accordingly, this temperature range is rather undesirable from the viewpoint of product uniformity regarding the carbon number distribution. On the other hand, HDO temperatures which are significantly lower than 280° C. tend to result in insufficient hydrodeoxygenation (so that more oxygen remains in the product) and/or require highly active (and expensive) catalyst systems or extremely high hydrogen pressures. Thus, from an economic point of view, HDO temperatures of 280° C. or more are highly favourable.

The present inventors now surprisingly found that by controlling the content of dimers having 4 oxygen atoms (4ox content) in the conversion product (and fed to the final HDO step) within the limits of the present invention, the further oligomerization can be suppressed to a certain degree while at the same time the number of naphthenic hydrocarbons can be reduced.

Thus, adjusting the 4ox content in the claimed range by higher pressure during the C—C coupling reaction in the conversion step (i.e. carrying out hydrotreatment simultaneously with the C—C coupling reaction) and/or using a mild hydrogenation/preliminary HDO reaction (i.e. carrying out hydrotreatment after the C—C coupling reaction) prior the final (full) HDO, allows using higher HDO temperatures, thus facilitating the final HDO process and leading to HDO products which are virtually oxygen-free (i.e. having a total oxygen content of less than 1.0 wt-%, preferably less than 0.5 wt-% or less than 0.1 wt-%).

Using the approach of the present invention, even higher temperatures as mentioned above may thus be employed in the final HDO reaction while still avoiding undesired side-reactions. Further, the present inventors found that the higher the temperature in the final HDO reaction, the higher is the density of the resulting HDO product. Higher density may be caused by cyclisation/aromatisation/oligomerization reactions during high temperature HDO.

In the present invention, the levulinic acid or a levulinic acid ester is preferred as a feed.

The method of the present invention preferably further comprises a separation step of removing unreacted levulinic acid before the final hydrodeoxygenation step.

Under practical reaction conditions, the dimerization reaction reaches a turnover of levulinic acid of about 50% by weight. Thus, about 50% by weight of the product of the C—C-coupling reaction consist of unreacted levulinic acid (monomer). This monomer is preferably removed prior to the final HDO step. If the hydrotreatment in the conversion step is carried out (at least partially) after the C—C coupling reaction, it is preferable to remove the unreacted levulinic acid before the hydrotreatment. Most suitably, the monomer is removed immediately after the C—C-coupling reaction. Vacuum distillation is a suitable method for removing the monomer, due to the observation, if the distillation temperature is too high, further (thermal) C—C-coupling reaction may occur (due to the usually high reactivity of the levulinic acid dimers/oligomers). On the other hand, since the 4ox content is adjusted with the limits of the present invention, good monomer removal rates can be achieved with distillation while the degree of further cyclisation, oligomerization reactions remains low.

Accordingly, the monomer removal is preferably carried out after the 4ox content is adjusted within the limits of the present invention.

Specifically, the C—C-coupling reaction product may be fractionated to remove potential unreacted levulinic acid monomers and other light components such as water, γ-valerolactone (GVL) and $CO_2$ formed in the C—C-coupling. The unreacted levulinic acid (monomer) may be recycled and combined with the feedstock.

According to one embodiment of the present invention, the 4ox content is adjusted by performing a mild hydrogenation after completion of the C—C-coupling reaction, i.e. the hydrotreatment in the conversion step is carried out (at least partially) after completion of the C—C-coupling reaction.

In a preferred embodiment, the conversion step comprises a condensation step of subjecting the feedstock to the C—C coupling reaction so as to produce a condensation product containing levulinic acid dimers/oligomers, and a mild hydrogenation step of subjecting at least the levulinic acid dimers to hydrogenation at a temperature of 270° C. or less, preferably 250° C. or less, so as to produce the conversion product.

Using this mild hydrogenation reaction, mainly the more reactive keto groups in the condensation product (C—C-coupling reaction product) and double bonds are hydrogenated. Accordingly, the 4ox content in the feed of the final HDO step is increased and the oligomerization tendency as well as the likelihood of side reactions is decreased.

In this embodiment, the condensation step may be carried out under a hydrogen ($H_2$) pressure of 20 bar (absolute) or more. In this case, the 4ox content can be already increased in the condensation step (if no hydrotreatment is carried out in the conversion step, the theoretical 4ox content is approximately 0). Further, a high hydrogen pressure in the condensation step stabilizes the performance of the IER catalyst and shifts the condensation product from lactone form to diacid form. The hydrogen pressure is preferably 22 bar or more, more preferably 25 bar or more, or 30 bar or more. The hydrogen pressure has no upper limit regarding the effects of the present invention. However, from the viewpoint of practicability and efficiency, the hydrogen pressure is preferably 100 bar or less, more preferably 70 bar or less, further preferably 60 bar or less. The pressure is particularly preferably in the range of 20 to 50 bar.

Unless explicitly stated, the pressure values in the present invention relate to absolute pressures. Further, when speaking of hydrogen pressure or pressure of a specific gas in general, the partial pressure of hydrogen (or the specified gas) is meant.

In the conversion step, the C—C-coupling step, the (preliminary/mild) hydrogenation step and/or the final HDO step, the hydrogen may be mixed with one or more other gases (dilution gas), preferably an inert gas such as nitrogen, argon, helium or another of the noble gases, or gas behaving inertly to the reaction conditions of the present invention. By behaving inertly it is meant that the gas should not to a major extent participate as a chemical reaction member, and preferably the inert gas should participate as little as possible, such as not participate at all. It is also possible that no dilution gas is added.

On the other hand, the condensation step (the C—C coupling reaction) may be carried out under a hydrogen ($H_2$) pressure of less than 25 bar (absolute), more preferably less than 20 bar, even more preferably less than 15 bar, less than 10 bar, less than 5. The hydrogen pressure may particularly be in the range of 1 to 20 bar.

The use of hydrogen in the condensation step stabilizes the performance of the IER catalyst. However, a high hydrogen pressure decreases the amount of LA converted to trimers, which trimers are, however, particularly preferable for diesel applications. High pressure increases costs and requires more complicated (high pressure) reactors. Since the 4ox content can also be sufficiently increased by the (mild/preliminary) hydrogenation step, it is thus not necessary to use high a hydrogen pressure in the C—C-coupling step. From a LA-trimer/LA-oligomer production point of view, using a low hydrogen pressure is therefore favourable.

According to another embodiment of the present invention, the 4ox content may be adjusted within the limits of the present invention by using a high hydrogen pressure in the C—C-coupling step. In this case, it is not necessary to carry out a mild hydrogenation as mentioned above and it is preferred that no mild hydrogenation is carried out after the C—C-coupling step and before the final HDO step.

In a preferred embodiment, the conversion step comprises a condensation step of subjecting the feedstock to the C—C-coupling reaction under a hydrogen ($H_2$) pressure of preferably 25 bar (absolute) or more, more preferably 35 bar or more, 40 bar or more, 45 bar or more, or 50 bar or more.

When no further (mild) hydrogenation is carried out, the C—C-coupling reaction thus directly results in a conversion product which is suitable for final (full) HDO.

While a high hydrogen pressure in the C—C-coupling step requires more sophisticated equipment, it is nevertheless possible to omit the mild hydrogenation step since the adjustment of the 4ox content is already achieved in the C—C-coupling step. Furthermore, a high hydrogen pressure in the C—C-coupling step was surprisingly found to shift the C—C-coupling reaction product (dimer) from the lactone form to the diacid form. Since the lactone form dimers tend to result in naphthenic or aromatic products after final HDO, this embodiment is particularly suitable for the production of gasoline, JET fuel components and chemical components.

The hydrogen pressure in this embodiment of the C—C-coupling step may be at least 20 bar, preferably at least 22 bar, more preferably at least 25 bar, or in the range of 20 to 50 bar. However, the upper hydrogen pressure is not necessarily limited and may be 200 bar or less, 100 bar or less, 80 bar or less, 70 bar or less, or 60 bar or less.

In the present invention, the hydrogenating metal is preferably selected from metals of the Group VIII of the Periodic Table of Elements, more preferably Co, Ni, Ru, Rh, Pd, and Pt, further preferably Pd, or a combination of two or more of these.

These metals, in particular Pd, has been found to provide good hydrogenation properties and being well compatible with the requirements of the C—C-coupling reaction using an IER.

Preferably, the C—C-coupling reaction is conducted at a temperature in the range of 100-200° C., preferably 120-180° C., more preferably 120-160° C., most preferably 120-140° C. This temperature range was found to be particularly suitable for obtaining a high yield of levulinic acid dimers (or dimer derivatives) which are suitable to be used in the next step(s) of the method.

In the C—C-coupling reaction, the at least one levulinic acid reacts with another levulinic acid or levulinic acid derivative under the formation of a new carbon-carbon bond in the condensation product. In other words, the molecular weight of the levulinic acid is increased using the levulinic acid as a direct precursor (one-step reaction) and within a single reactor or a single catalyst bed.

The C—C-coupling reaction can be controlled by adjusting several parameters, including by selection of reaction conditions such as weight hourly space velocity (WHSV) (kg feedstock/kg catalyst per hour).

Preferably the C—C-coupling reaction is conducted at a weight hourly space velocity (kg feedstock/kg catalyst*hour) of 0.05 $h^{-1}$ to 2.0 $h^{-1}$, preferably 0.1 $h^{-1}$ to 1.8 $h^{-1}$, more preferably 0.2 $h^{-1}$ to 1.5 $h^{-1}$, most preferably 0.25 $h^{-1}$ to 1.25 $h^{-1}$. The WHSV has an influence on the composition of the resulting material, since it determines the effective contact time of reagent and catalyst. The above-mentioned ranges have shown to provide a high degree of favourable products.

Preferably, the C—C-coupling reactions are conducted at a flow ratio ($H_2$/feedstock) of 100-3000 Nl/l, preferably 200-2000 Nl/l, more preferably 500-1800 Nl/l and most preferably 500-1500 Nl/l.

The feedstock may be obtained from processing of lignocellulosic material, and such processed material may be used directly, or purified to varying degrees before being used as a feedstock in the method of the present invention. The levulinic acid may be produced e.g. with the Biofine method disclosed in U.S. Pat. No. 5,608,105.

One of the advantages of the present invention is that levulinic acid produced from renewable materials can be upgraded to higher molecular weight hydrocarbons and/or hydrocarbon derivatives, which may be used as fuel or base oil components or chemicals or as starting components in the production of fuel or base oil components or chemicals.

Preferably, in the final hydrodeoxygenation step, a HDO catalyst is employed which comprises a metal having hydrogenation catalyst function on a support, such as for example a HDO catalyst metal selected from a group consisting of Pd, Pt, Ni, Co, Mo, Ru, Rh, W or any combination of these. The metal having hydrogenation catalyst function may be carried on a support, preferably an inorganic oxide support, more preferably silica, alumina, titania, zirconia, carbon or a combination thereof. A highly preferable HDO catalyst comprises sulfided NiMo, which is preferably supported on an inorganic oxide such as alumina.

The final hydrodeoxygenation step may be conducted at a temperature of up to 500° C. and at a hydrogen pressure of 10-150 bar.

Water and light gases may be separated from the HDO product with any conventional means such as distillation. After the removal of water and light gases, the HDO product may be fractionated to one or more fractions suitable for use as gasoline, aviation fuel, diesel or base oil components.

Preferably, the method of the present invention comprises a fractionation step of fractionating the HDO product. The fractionation may be conducted by any conventional means, such as distillation. Optionally, part of the product of the final HDO step may be recycled to and combined with the feed of the reactor for final HDO.

The method of the present invention may be carried out in a reactor, such as a stirred tank reactor, preferably a continuous stirred tank reactor, or a tubular flow reactor, preferably a continuous flow reactor. Further, the individual steps of the present invention may be carried out in the same reactor or in different reactors.

Preferably, the conversion step and the final (full) HDO step are carried out in different reactors. When the conversion step comprises a C—C-coupling step and a preliminary hydrogenation step, these steps may be carried out in the same or in different reactors, wherein, in the latter case, the preliminary hydrogenation step may be carried out in the same reactor as the final HDO step (one after another). When the preliminary hydrogenation step and the final HDO step are carried out in the same reactor, the mild hydrogenation/HDO catalyst is preferably a NiMo catalyst (sulfided NiMo catalyst). When the C—C-coupling step, the preliminary hydrogenation step and/or the HDO step are carried out in different reactors, the catalyst for preliminary (mild) hydrogenation (hydrotreatment) is preferably a noble metal based catalyst, such as a Pd-based catalyst or a Pt-based catalyst, or a NiMo catalyst and the catalyst for final HDO may be a noble metal catalyst or a NiMo catalyst, preferably a NiMo catalyst. In any case, it is preferred that the catalyst for mild hydrogenation be a noble metal catalyst when the catalyst for final HDO is a noble metal catalyst.

The hydrogenation catalyst employed in the hydrogenation treatment (preliminary hydrogenation/preliminary HDO) may be the same as the catalyst employed in the final HDO step.

The product of the final hydrodeoxygenation step may also be subjected to an isomerization step in the presence of hydrogen and an isomerization catalyst. Both the final hydrodeoxygenation step and isomerisation step may be conducted in the same reactor. In some embodiments the isomerisation catalyst is a noble metal bifunctional catalyst, for example Pt-SAPO or Pt-ZSM-catalyst. The isomerization step may for example be conducted at a temperature of 200-400° C. and at a pressure of 20-150 bar. Fractionation may be carried out before or after isomerization, but is preferably carried out after isomerization.

A further embodiment of the present invention relates to a method of controlling the ratio (lac/dia) of lactone type dimers (lac) to diacid type dimers (dia), wherein the method comprises a step of subjecting a feedstock comprising at least levulinic acid to a C—C coupling reaction, wherein the C—C coupling reaction is carried out using an acidic ion exchange resin carrying a hydrogenating metal as a catalyst and in the presence of hydrogen, a step of determining the ratio lac/dia of in the C—C-coupling product, and a step of repeating the C—C-coupling reaction while adjusting the hydrogen pressure used for the C—C-coupling reaction depending on the deviation of the ratio lac/dia from a desired ratio.

Carboxylic acids are useful in industrial applications directly or indirectly through acid halides, esters, salts, and anhydride forms, polymerization, etc. Dicarboxylic acids can yield two kinds of salts or esters, as they contain two carboxyl groups in one molecule. These are useful in a large variety of industrial applications including: plasticizer for polymers, biodegradable solvents and lubricants, engineering plastics, epoxy curing agent, adhesive and powder coating, corrosion inhibitor, perfumery and pharmaceutical, electrolyte, etc.

Figure 1:
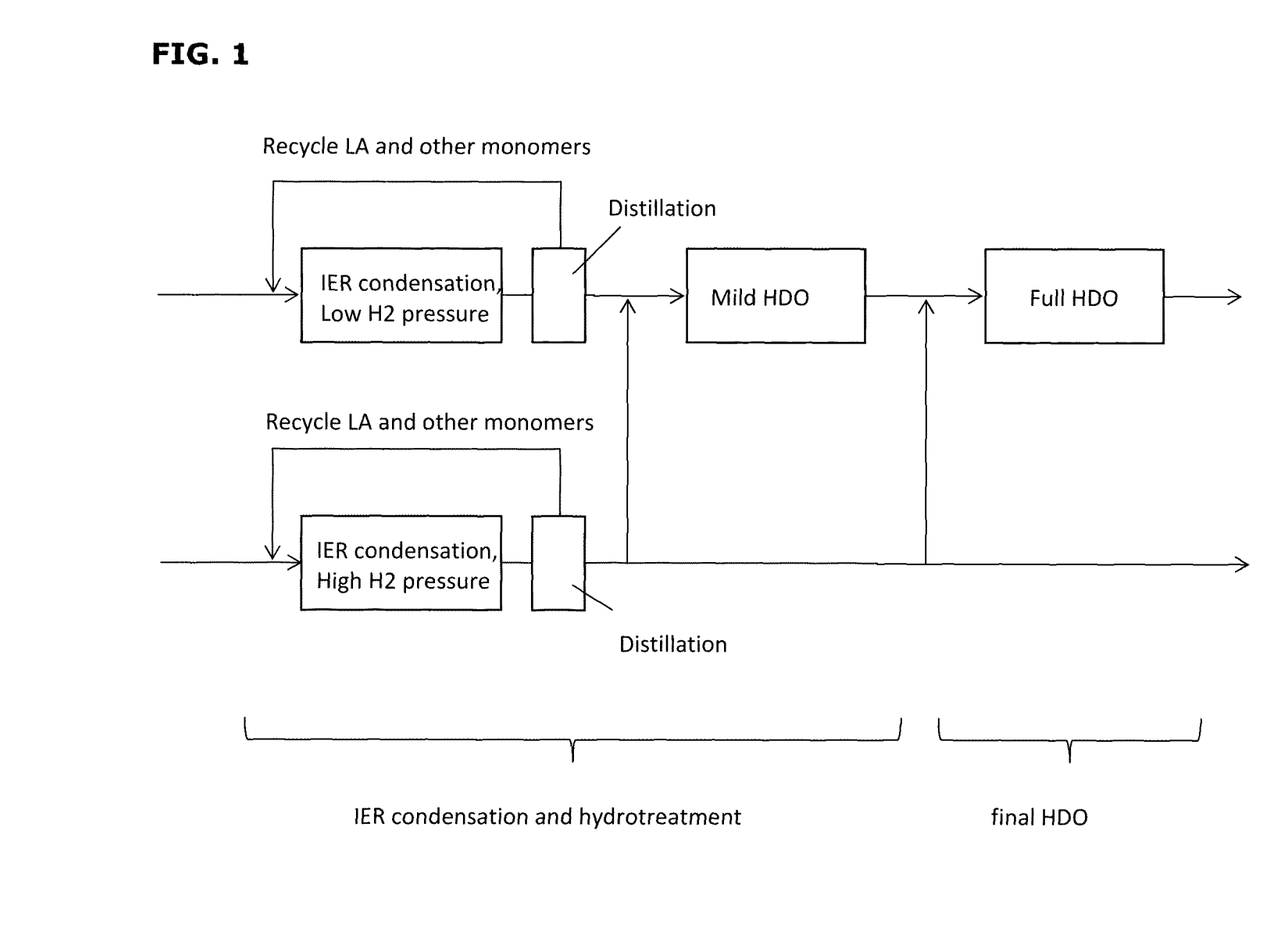
FIG. 1 is a flow chart illustrating embodiments of the method of the present invention.
Figure 2:
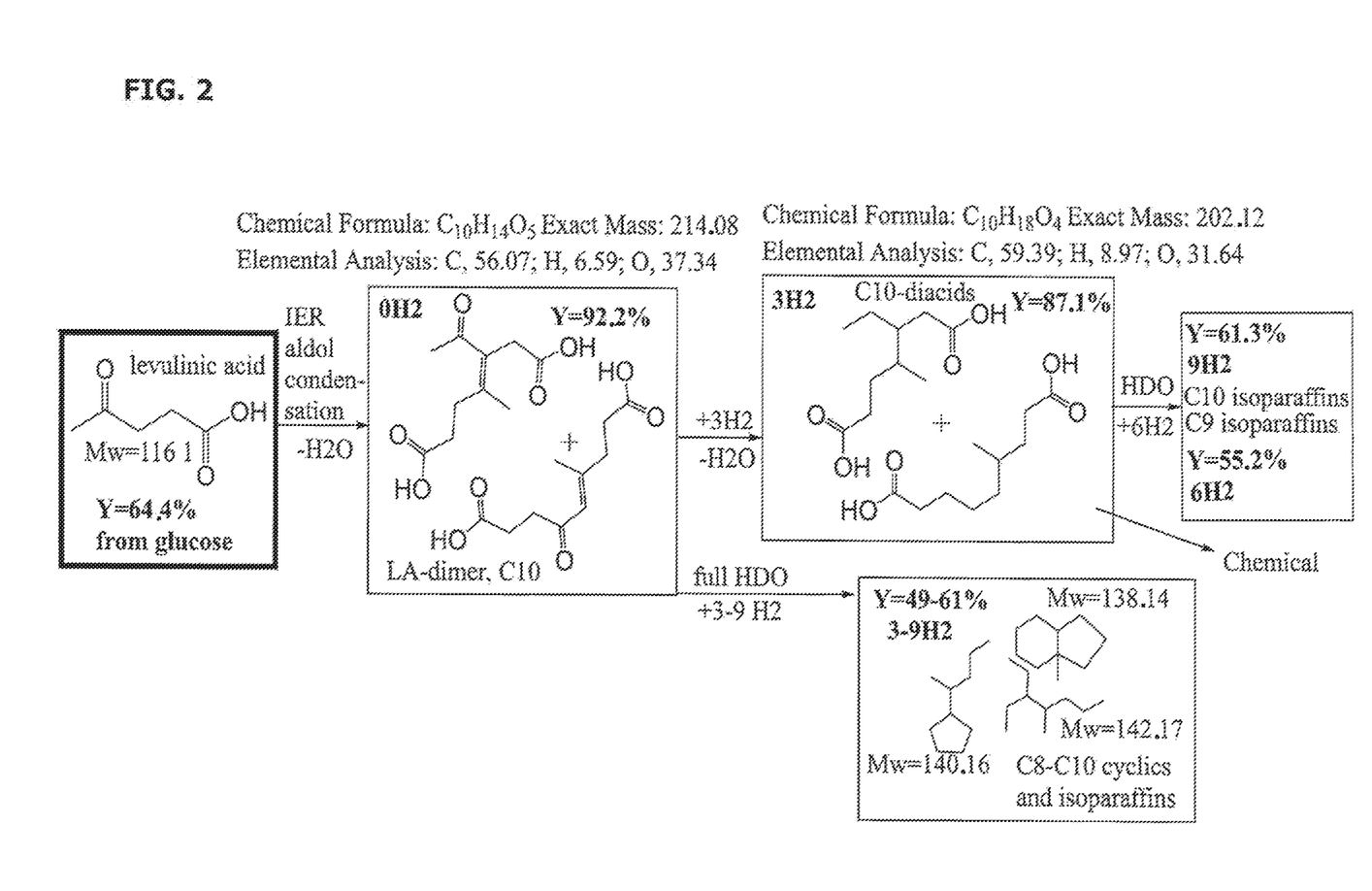
FIG. 2 is a flow chart showing levulinic acid reaction products via LA dimer intermediates and theoretical yield of the respective reactions.
Figure 3:
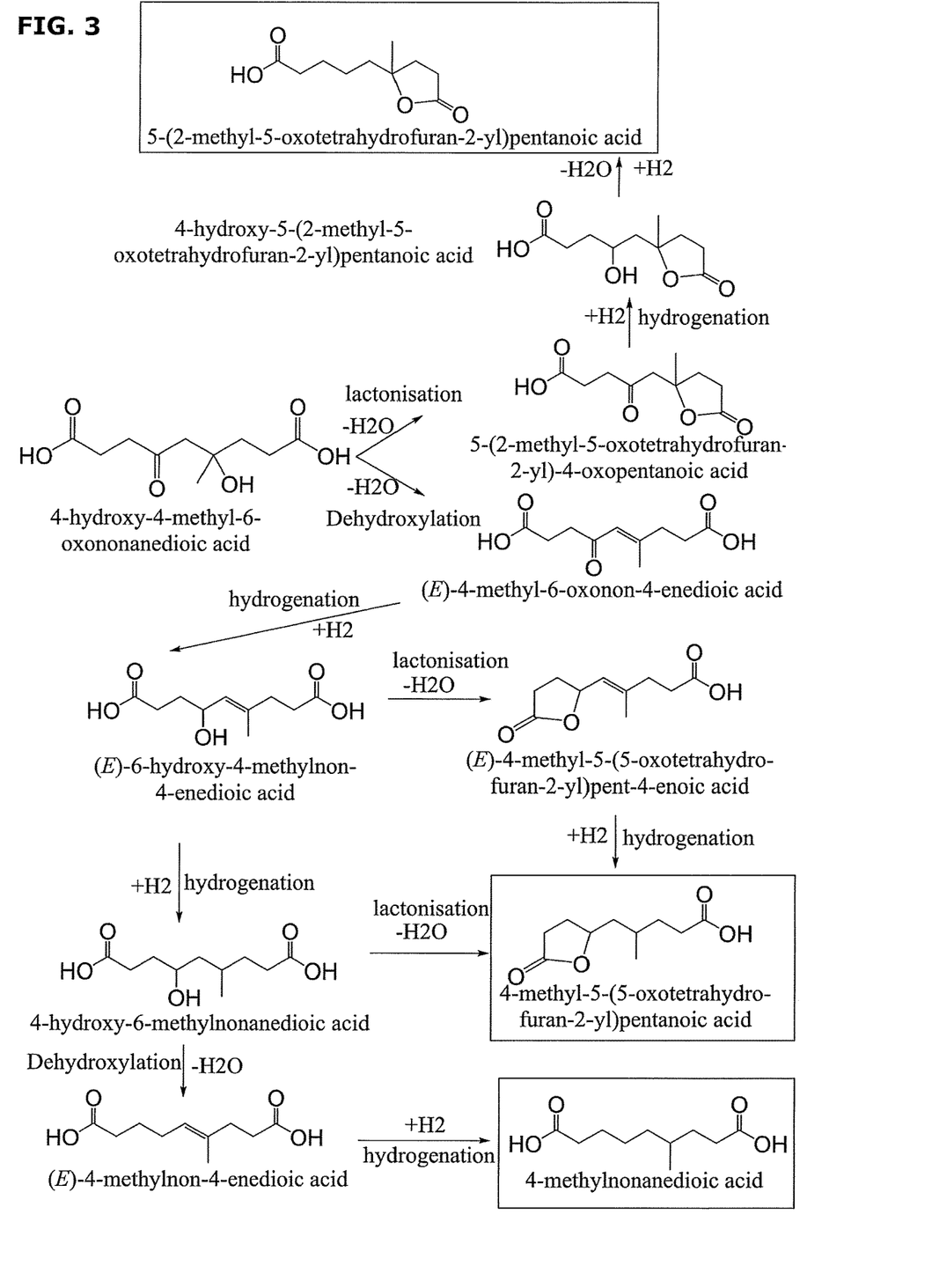
FIG. 3 shows the hydrogenation reaction chemistry of 4-hydroxy-4-methyl-6-oxononanedioic acid (a non-stable LA dimer).
Figure 4:
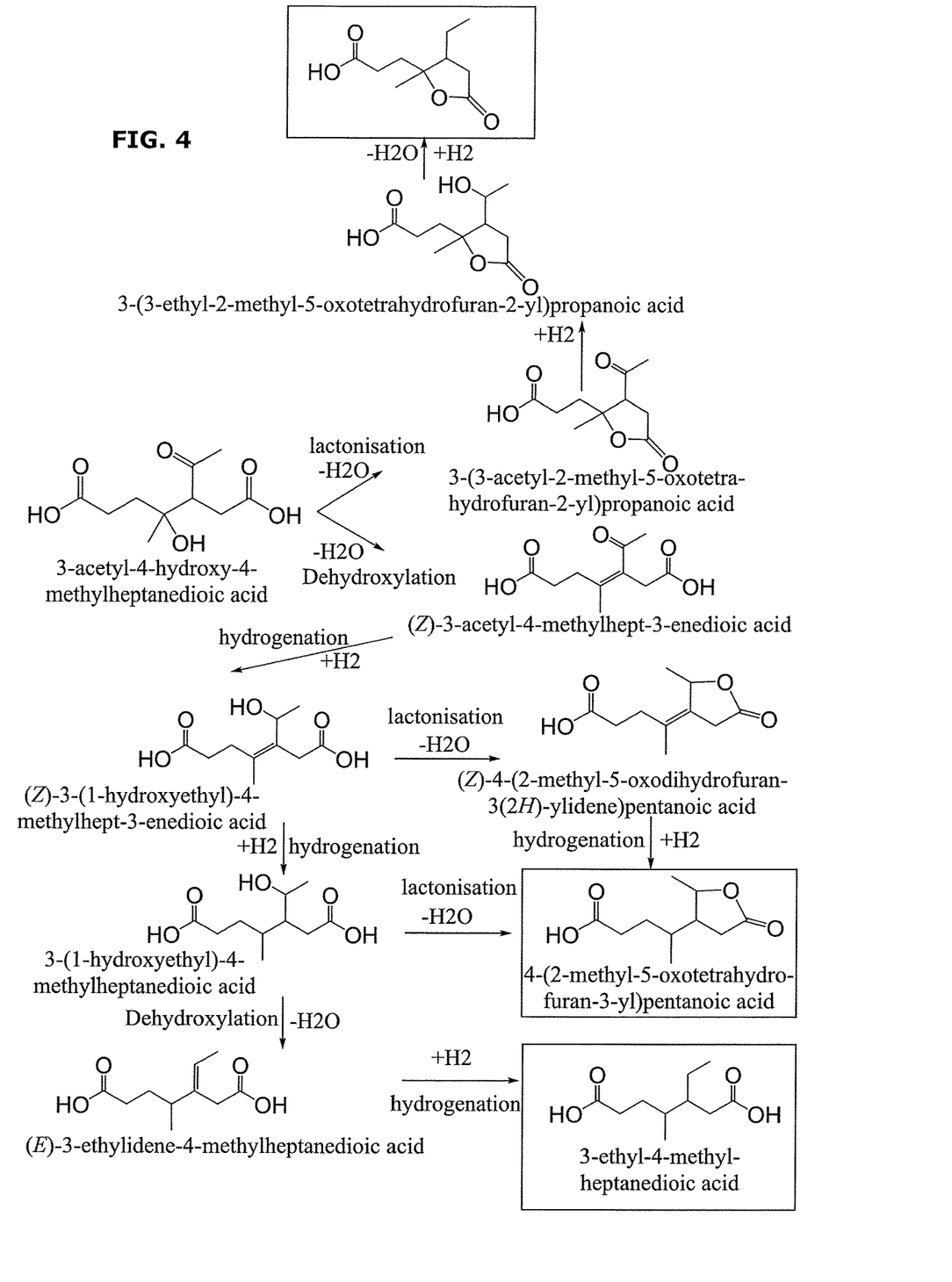
FIG. 4 shows the hydrogenation reaction chemistry of 3-acetyl-4-hydroxy-4-methylheptanedioic acid (a non-stable LA dimer).
Figure 5:
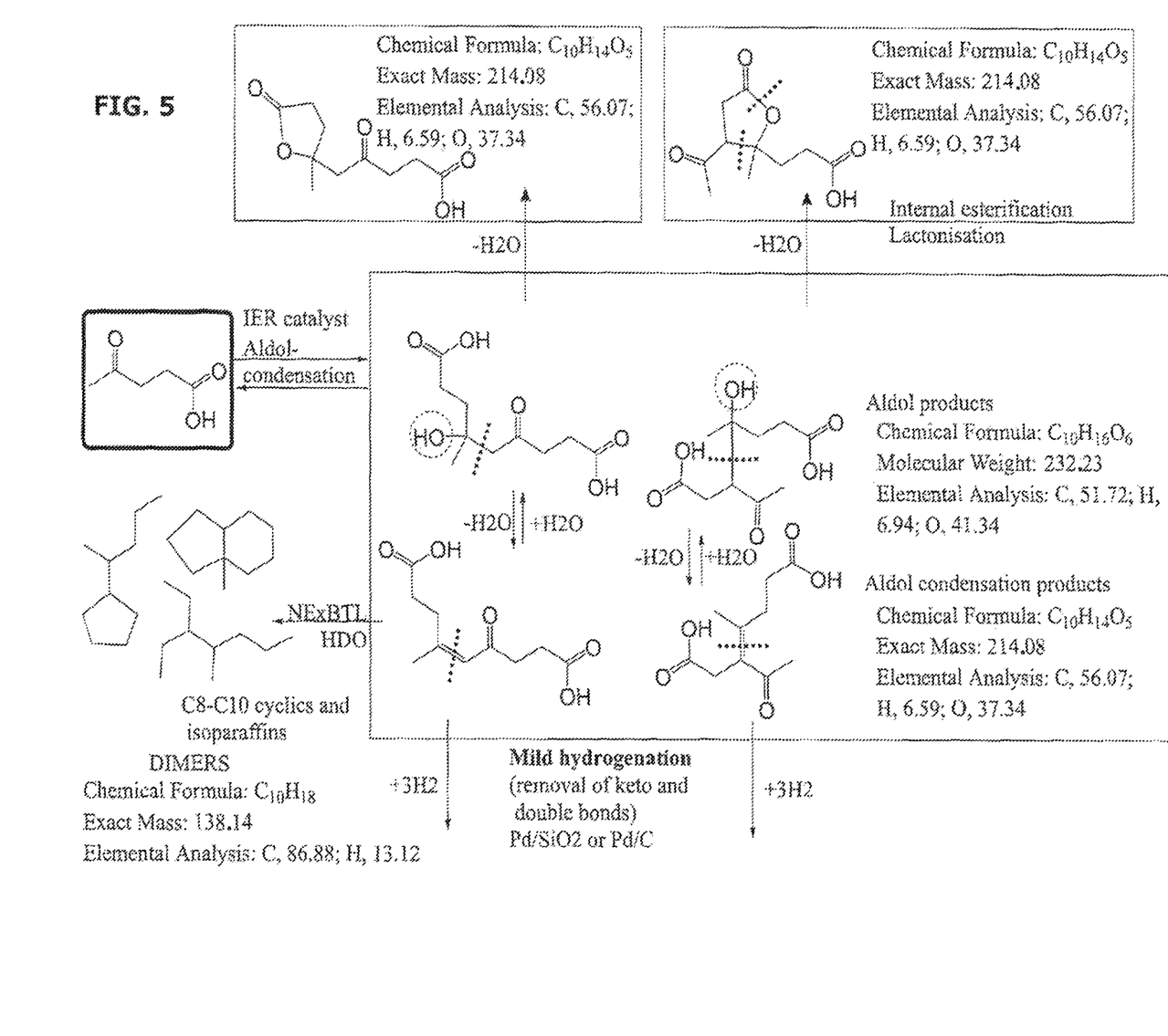
FIGS. 5 and 6 illustrate the value addition chain of LA via LA dimers
Figure 6:
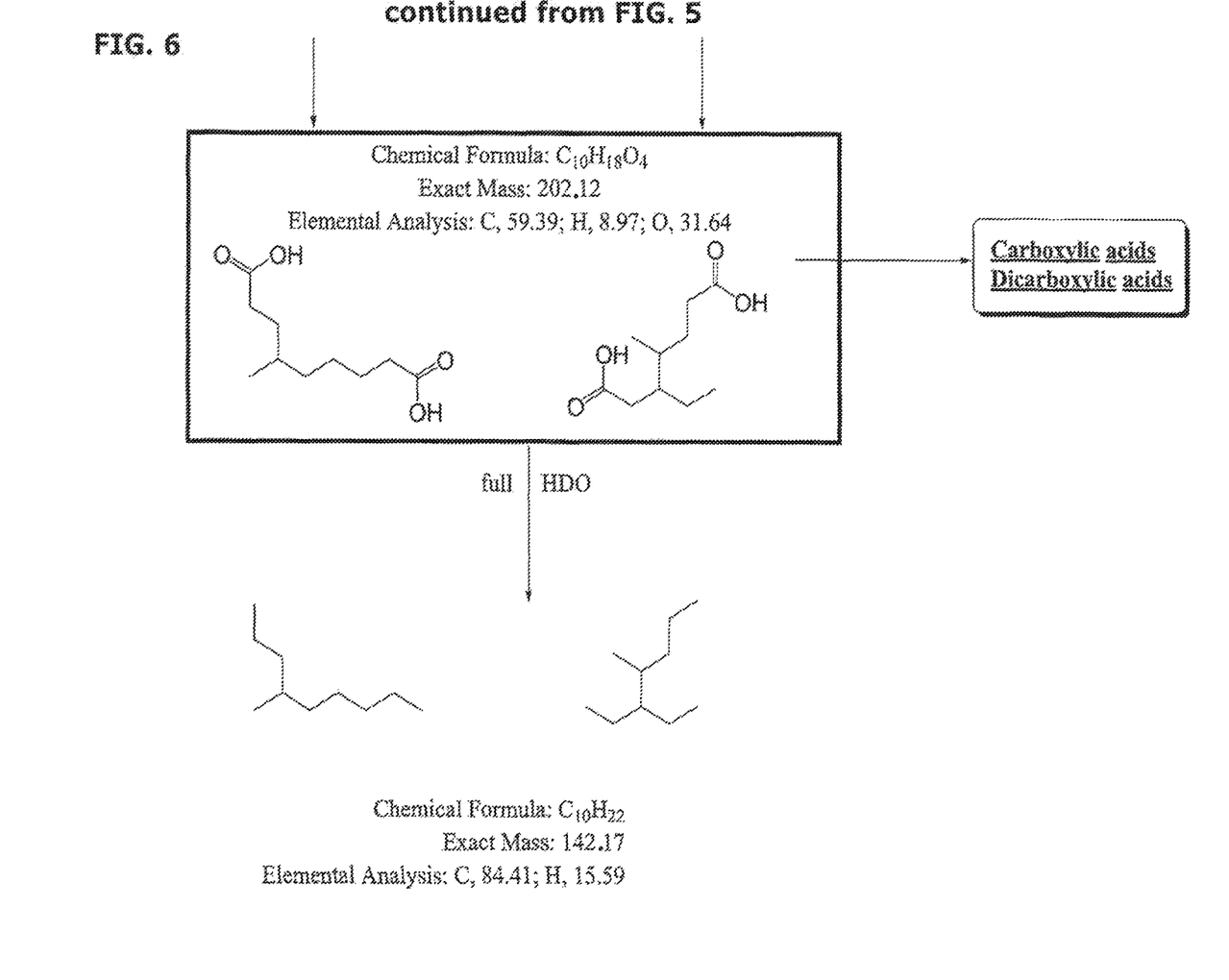

Levulinic acid aldol condensation forms several dimeric acids or their esters shown in FIG. 5. These diacids/diesters can be used in the applications mentioned above. Direct HDO of these acids produces cyclic hydrocarbon fuel components and selective mild HDO produces linear diacids which can be used as chemicals and subsequent final full HDO produces isoparaffinic fuel components.

Preferably, the hydrogen pressure is increased when the ratio lac/dia is higher than a desired ratio and the hydrogen pressure is decreased when the ratio lac/dia is lower than a desired ratio. The type and properties of the IER catalyst, the hydrogenating metal, the type and amount of levulinic acid, the feedstock, the reaction temperatures and the amount of type of additional components in the feedstock or added to the feedstock may be the same as in the conversion step and/or the C—C-coupling step referred to in the first-mentioned method of the present invention.

In a further embodiment, the present invention relates to a method for conversion of levulinic acid, wherein the method comprises a step of providing a feedstock comprising at least levulinic acid, a conversion step of subjecting the feedstock to a C—C coupling reaction, wherein the C—C coupling reaction is carried out using an acidic ion exchange resin carrying a hydrogenating metal as a catalyst and under a hydrogen pressure of 3 bar (absolute) or less.

The type and properties of the IER catalyst, the hydrogenating metal, the feedstock, the reaction temperatures and the amount of type of additional components in the feedstock or added to the feedstock may be the same as in the conversion step and/or the C—C-coupling step referred to in the first-mentioned method of the present invention.

The method of this embodiment of the present invention provides a C—C-coupling product in which the majority (i.e. 50% by weight or more) of the levulinic acid dimers are present in lactone form. Thus, this method provides a suitable method for producing lactone type levulinic acid dimers which can be used in chemical industry. The present invention furthermore relates to the reaction products obtained by the method of this embodiment, be it as a product mixture or as pure product after purification.

In a further embodiment, the present invention relates to a method for conversion of levulinic acid comprising a step of providing a feedstock comprising at least levulinic acid, a conversion step of subjecting the feedstock to a C—C coupling reaction, wherein the C—C coupling reaction is carried out using an acidic ion exchange resin carrying a hydrogenating metal as a catalyst and under a hydrogen pressure of 40 bar (absolute) or more.

The method of this embodiment of the present invention provides a C—C-coupling product in which the majority (i.e. 50% by weight or more) of the levulinic acid dimers are present in diacid form. Due to the high hydrogen pressure, the diacid dimers may further be partially hydrogenated (dehydroxylated). Thus, this method provides a suitable method for producing diacid type levulinic acid dimers and dimer derivatives which can be used in chemical industry. The present invention furthermore relates to the reaction products obtained by the method of this embodiment, be it as a product mixture or as pure product after purification. Specifically, this method may be used for the production of 3-ethyl-4-methylheptanedioic acid or 4-methylnonanedioic acid, which may be used as a low cost renewable substitute for sebacic acid and its analogues.

In another aspect of the present invention, a hydrocarbon composition obtainable by the method(s) according to the present invention is provided. This product may be directly used as fuel or base oil components or chemicals or as intermediate components in production of fuel or base oil components or chemicals. Preferably, the hydrocarbon composition obtained after fractionating the HDO product is used, most suitably as gasoline fuel (component), diesel fuel (component) or jet fuel (component).

EXAMPLES

Reference Example 1

A feedstock containing 98 wt.-parts commercial grade levulinic acid (97 wt.-% purity) and 2 wt.-parts water was provided. The feedstock and hydrogen were fed to a tubular reactor supporting Amberlyst CH-34 catalyst (trade name; Pd doped ion exchange resin). The temperature in the reactor was adjusted to 130° C., the hydrogen pressure was 20 bar, WHSV was 0.2 h$^{-1}$ and hydrogen to feedstock (liquid raw material) flow ratio was 1170 Nl/l.

The conversion product obtained after the tubular reactor contained 44 wt.-% non-reacted levulinic acid (LA) and γ-valerolactone (GVL), 53 wt.-% dimers and about 2 wt.-% oligomers. The non-reacted LA (+GVL) were separated by distillation.

Before final HDO, the distilled product (conversion product) had a saturated 4ox dimer content of 13.8 wt.-%.

The conversion product was subjected to final HDO in a tubular reactor at a hydrogen pressure of 80 bar, a temperature of 306° C., WHSV of 0.3 h$^{-1}$, a sulfided NiMo hydrogenation catalyst supported on alumina and a flow rate of hydrogen to conversion product of 2100 Nl/l.

The HDO product was fractionated and the compositions of gasoline and diesel fractions were evaluated. The results are shown in Table 1.

Further, it was found that the HDO product contained at least 5 wt.-% of hydrocarbons derived from levulinic acid trimers.

TABLE 1

| Gasoline fraction and diesel fraction | |
|---|---|
| C-C-coupling reaction temperature | Example 1<br>130° C. |
| Gasoline fraction | |
| Paraffins | 32.2 wt.-% |
| Naphthenes | 66.2 wt.-% |
| Aromatics | 1.5 wt.-% |
| Diesel fraction | |
| Aromatics | 11.8 wt.-% |

As can be seen, the content of aromatics in the gasoline and diesel fractions is significantly lower than for any oligomerization reaction using oxide catalyst or using no catalyst.

Examples 1 to 3

Effects on the content of 4ox saturated LA dimer derivatives resulting from low and high hydrogen pressure during the aldol condensation and final hydrogenation over NiMo and Pd/C catalysts was evaluated. The aldol condensation reaction of Reference Example 1 was repeated with a hydrogen pressure of 20 bar (Examples 2 and 3) and 50 bar (Example 1).

By regulating the hydrogen pressure during aldol condensation it was possible to vary the formation of 4ox saturated dimers (cf. Table 2). By increasing the pressure from 20 bar to 50 bar a relative increase of about 9% points of 4ox saturated dimers was achieved.

TABLE 2

Fraction of 4ox saturated dimers formed after low and high pressure aldol condensation.

| | | Dimers area-%/wt.-% (from total dimer-area) | |
|---|---|---|---|
| Structures | Description | Low pressure (20 bar) aldol condensation | High pressure (50 bar) aldol condensation |
| 1, 2* | 4ox saturated dimer | 13.8 | 22.2 |

*including skeletal isomers (cf. formulas below)

The low pressure aldol condensation product was further subjected to mild hydrogenation over NiMo (Example 2) and Pd/C (Example 3) catalyst at a reaction temperature of 250° C. The total amount of 4ox saturated dimers increased from 13.8 wt.-% to over 30 wt.-% (cf. Table 3).

TABLE 3

Fraction of 4ox saturated dimers after mild hydrogenation

| | | Dimers area-%/wt.-% (from total dimer-area) | |
|---|---|---|---|
| Structures | Description | NiMo (Example 2) | Pd/C (Example 3) |
| 1, 2* | 4ox saturated dimer | 32.1 | 37.8 |

*including skeletal isomers (cf. formulas below)

1)

2)

Example 4

The influence of hydrogen pressure during aldol condensation (i.e. hydrotreatment during the C—C coupling reaction) on the formation of cyclic compounds during final HDO of dimers was evaluated in Example 4.

When preparing dimer solutions over IER-catalyst at 130° C. at various hydrogen pressures (1, 20 and 50 bar) it was observed that by increasing the pressure

- the content of levulinic acid dimer derivatives having 4 oxygen atoms and no C═C bonds (4ox, no C═C) increased, and
- the fraction of diacid dimers in the dimer solution produced increased (cf. Table 4). Oxygen removal corresponding to that in mild-HDO occurred. The diacid-to-lactone dimer ratio was tuneable by the hydrogen pressure used.

TABLE 4

Relative amount of 4ox (no C═C) dimers and fraction of diacid dimers in dimer solution produced at various hydrogen pressures.

| Hydrogen pressure, bar | Increase in the amount of 4ox (no C═C) dimers relative to amount obtained at 1 bar | Fraction of diacid dimers in dimer solution |
|---|---|---|
| 1 | 1 | 30 wt.-% |
| 20 | 5 | 90 wt.-% |
| 50 | 14 | 91 wt.-% |

When subjecting dimer-solutions (conversion products) prepared at various hydrogen pressures to final HDO it was noticed that less cyclic compounds were formed from a dimer solution prepared under a hydrogen pressure of 50 bar compared to the dimer solution prepared at 1 bar (cf. Table 5). Prior to final HDO the dimer solution prepared at 50 bar was composed mainly of diacid-type dimers (structure 2 above) and contained less oxygen compared to the dimer solution formed at 1 bar which was mainly composed of lactone-type dimers (structure 1 above).

TABLE 5

Difference in amount of cyclic compounds formed during final HDO (310° C., NiMo catalyst) of feed containing different amounts of oxygen and different types of dimers. Diacid dimer feed-solution contains less oxygen, in the form of carbonyl groups, compared to the lactone dimer feed-solution.

| Feed | final HDO products, 310° C., 80 bar [GC-area, a.u.] | | |
|---|---|---|---|
| | Benzene | Indane | Trimethyl-dihydrobenzaldehyde |
| Diacid dimers (high pressure aldol-condensation) | 1734413 | 1745989 | 129166 |
| Lactone dimers (low pressure aldol-condensation) | 3182095 | 3983340 | 237942 |
| Diacid/Lactone Product ratio [%] | 54 | 44 | 54 |

As can be seen, high pressure in the C—C coupling reaction gives less oxygen and less lactone-type dimers—both shown to be beneficial properties to decrease thermal cyclisation reactions during the final HDO step.

Example 5 and Comparative Example 1

A C—C-coupling reaction was performed in the same manner as for Reference Example 1. The C—C-coupling reaction product was obtained after the content of the tubular reactor was distilled in the same manner as in Reference Example 1 to remove unreacted components.

Preliminary (mild) hydrogenation was carried out in a tubular reactor at 253° C., as shown in Table 6, and at reactor pressure of 50 bar, WHSV of 0.5 h$^{-1}$, with a sulfided NiMo hydrogenation catalyst supported on alumina. Hydrogen/oil (distilled C—C coupling reaction product) volume ratio was 3000 normal-liters H$_2$/liter oil.

After the preliminary hydrogenation, the final HDO of product was done at a reaction temperature of 310° C. using the same catalyst system as in the preliminary hydrogenation step (sulfided NiMo supported on alumina). Reactor pressure was 50 bars and WHSV 0.5 h$^{-1}$. Hydrogen remaining in the 1$^{st}$ reactor was directly forwarded to the second reactor together with the product of the preliminary hydrogenation and used for the final HDO reaction (Example 5).

The same procedure was repeated for Comparative Example 1, except for using the same temperature in the 1$^{st}$ and the 2$^{nd}$ hydrogenation reactor, thus simulating a direct final (full) HDO reaction.

Products obtained by final HDO were distilled to IBP (initial boiling point)—180° C.-fraction and Paraffin (P)/Naphthene (N)-ratio and decarboxylation ratios were calculated from GC-MS-analysis.

It is clearly seen from table 6 that preliminary hydrogenation significantly raises the P/N-ratio (lower the cyclisation of product molecules during final HDO).

From the GHG reduction potential point of view, decarboxylation ratios of C10 LA dimers were surprisingly high and improve the preliminary GHG reduction potential value over 60%. It has to be remembered that decarboxylation increases with more severe HDO temperature conditions, but also the harmful side reactions like cyclisation, aromatisation and phenol formation. Therefore even though direct (final) HDO achieves higher decarboxylation ratios, it is not preferred, due to the other side reactions, which decrease the quality of fuel.

TABLE 6

| | Ex. 5 Two-step HDO | Comp. Ex. 1 Direct HDO |
|---|---|---|
| 4-ox content after LA condensation step | 13.8 wt.-% | 13.8 wt.-% |
| 1$^{st}$ (mild) HDO/HYD reactor/° C. | 253 | 309 |
| Pressure/bars | 50 | 50 |
| H$_2$/Oil (NLH$_2$/I oil) | 3000 | 3000 |
| WHSV, 1/h | 0.5 | 0.5 |
| 4-ox content after mild HDO/HYD | 32.1 wt.-% | — |
| Final HDO/HYD reactor/° C. | 310 | 308 |
| Pressure, bars | 50 | 50 |
| H$_2$/Oil, NL H$_2$/I oil | H$_2$ from 1st reactor | H$_2$ from 1st reactor |
| WHSV, 1/h | 0.50 | 0.50 |
| Paraffin/Naphthene-ratio | 0.41 | 0.21 |
| C8 Decarb-ratio of LA dimers, C8/(C8 + C9 + C10) | 10 wt.-% | 11 wt.-% |
| C9 Decarb-ratio of LA-dimers, C9/(C8 + C9 + C10) | 58 wt.-% | 69 wt.-% |
| Preliminary GHG reduction potential estimation value for fuel | >60% | >60% |

Examples 6 and Comparative Example 2

A C—C-coupling reaction was performed in the same manner as for Reference Example 1. The C—C-coupling reaction product was obtained after the content of the tubular reactor was distilled in the same manner as in Example 1 to remove unreacted components.

During a test run (Example 6) the C—C-coupling reaction product was subjected to preliminary hydrogenation/mild HDO with a Pd/C catalyst at 235° C., WHSV 1/h, using 50 bars reactor pressure and with H$_2$/Oil ratio 700 NL H$_2$/l oil. The conversion product was then fully hydrodeoxygenated at 310° C., 80 bars, WHSV 0.5 and H$_2$/oil ratio 2200.

During comparative test run (Comparative Example 1) the C—C-coupling reaction product was directly fully hydrotreated with a sulfided NiMo hydrogenation catalyst supported on alumina at 310° C., WHSV 0.26, using 80 bars reactor pressure and with H$_2$/Oil ratio 3000 NL H$_2$/l oil.

Products obtained were distilled to IBP (initial boiling point)—180° C. fraction. Paraffin/naphthene ratio and decarboxylation ratio, shown in table 7, were calculated from GC-MS-analysis.

It is clearly seen from table 7 that preliminary mild hydrogenation raises the P/N-ratio, which means less thermal cyclisation reactions during the final HDO step. This means better end-product properties for gasoline and especially diesel fuel. Blending RON (BRON) was analysed for both gasoline samples (cf. table 7). Two-step procedure increased the octane number by 5 octane units.

It is also seen that higher reactor pressure is beneficial for final hydrogenation (compared to results with final HDO at 50 bars, cf. table 7).

TABLE 7

| | Ex. 6 two-step | Comp. Ex. 2 Direct HDO |
|---|---|---|
| 4-ox content after LA condensation step | 13.8 wt.-% | 13.8 wt.-% |
| 1st (mild) HDO/HYD reactor | 235 | — |
| Pressure | 50 | — |
| H$_2$/Oil, NL H$_2$/I oil | 700 | — |
| WHSV | 1 | — |
| 4-ox content after mild HDO/HYD | 37.8 wt.-% | — |
| Final HDO/HYD reactor | 310 | 310 |
| Pressure | 80 | 80 |

TABLE 7-continued

|  | Ex. 6 two-step | Comp. Ex. 2 Direct HDO |
|---|---|---|
| H$_2$/Oil, NL H$_2$/l oil | 2200 | 3000 |
| WHSV | 0.50 | 0.26 |
| paraffin/naphthene-ratio | 0.88 | 0.49 |
| BRON | 61 | 56 |
| C8 Decarb-ratio of LA dimers, C8/(C8 + C9 + C10) | 5 wt.-% | 9 wt.-% |
| C9 Decarb-ratio of LA-dimers, C9/(C8 + C9 + C10) | 40 wt.-% | 54 wt.-% |
| Preliminary GHG reduction potential estimation value for fuel | >60% | >60% |

Comparative Example 3

In order to further verify the results of the present invention, sebacic acid was subjected to HDO and the resulting hydrocarbon product distribution was analyzed. Sebacic acid is a linear C10-dicarboxylic acid which is used as chemical as it is and as raw material for chemical derivatives. Diacids produced from levulinic acid condensation are diacids or acid lactones which have a keto group and a double bond in the middle of the diacid molecule. These structures have been found to form cyclic structures (naphthenes) during the HDO. In the present invention these more reactive structures are removed either by mild hydrogenation during the condensation (C—C coupling) step or during the extra mild hydrogenation/(preliminary) HDO step prior final full HDO of LA dimers.

In this comparative example, sebacic acid was directly hydrotreated to hydrocarbons under reaction conditions, which are needed for complete HDO. The test was done in a batch reactor using a temperature of 310° C. and 80 bars hydrogen pressure. Hydrogen flow was used through the reactor in order to remove produced water and CO2/CO.

Table 8 shows the product distribution and decarboxylation ratios.

It is seen that products other than n-paraffins are formed only in an amount of about 11 wt.-% and these compounds are mainly isomers of C8, C9 and C10 hydrocarbons (not only cyclic compounds). Therefore, it could be confirmed that cyclisation tendency is very small if ketones and double bonds are not present in molecule.

It is also clearly seen that the total decarboxylation ratio is rather high (only 23% C10 hydrocarbons is produced, the remainder was subject to decarboxylation to C8 or C9 species). Therefore GHG reduction potential will be >60% also in this case.

TABLE 8

The product distribution of direct HDO of sebacic acid

|  | Product distribution wt-% | Paraffin/naphthene ratio |
|---|---|---|
| Other C8-compounds | 2 |  |
| n-C8-paraffin | 25 | >12.5 |
| Other C9-compounds | 5 |  |
| n-C9-paraffin | 45 | >9 |
| Other C10-compounds | 4 |  |
| n-C10-paraffin | 19 | >4.8 |
| total | 100 | >8.1 |

TABLE 8-continued

The product distribution of direct HDO of sebacic acid

|  | Decarboxylation ratio |
|---|---|
| Total decarb. ratio (C9 + C8)/(C8 + C9 + C10) | 77 wt.-% |
| C8-decarb. ratio C8/(C8 + C9 + C10) | 27 wt.-% |
| C9-decarb. ratio C9/(C8 + C9 + C10) | 50 wt.-% |

The invention claimed is:

1. A method for conversion of levulinic acid comprising:
   providing a feedstock containing levulinic acid;
   a conversion step of subjecting the feedstock to a C—C coupling reaction, wherein the C—C coupling reaction is carried out using an acidic ion exchange resin carrying a hydrogenating metal, as a catalyst, and to a hydrotreatment so as to produce a product containing levulinic acid dimer derivatives having 4 oxygen atoms, wherein the hydrotreatment is carried out in a separate mild hydrodeoxygenation (HDO) step after the C—C coupling reaction at a temperature of from 235° C. to 270° C. so as to produce the product containing levulinic acid dimer derivatives having 4 oxygen atoms;
   adjustment of levulinic acid dimer derivatives having 4 oxygen atoms by performing a mild hydrogenation step after completion of the C—C coupling reaction and the mild HDO step; and
   a hydrodeoxygenation step of subjecting at least the levulinic acid dimer derivatives to a hydrodeoxygenation (HDO) reaction to produce a HDO product, wherein a content of levulinic acid dimer derivatives having 4 oxygen atoms relative to all levulinic acid dimer derivatives is 20 wt.-% or more, wherein the HDO product contains at least 5% by weight of hydrocarbons derived from levulinic acid trimers.

2. The method according to claim 1, wherein the content of levulinic acid dimer derivatives having 4 oxygen atoms and no carbon-carbon double bonds is 30 wt.-% or more based on the total amount of levulinic acid dimer derivatives having 4 oxygen atoms and/or the total content of levulinic acid dimer derivatives having 4 oxygen atoms and no carbon-carbon double bonds and levulinic acid dimer derivatives having 4 oxygen atoms and at least one carbon-carbon double bonds is 30 wt.-% or more based on the total amount of levulinic acid dimer derivatives having 4 oxygen atoms.

3. The method according to claim 2, wherein the hydrodeoxygenation (HDO) reaction is carried out at a temperature of at least 290° C.

4. The method according to claim 2, wherein the C—C coupling reaction is carried out in the presence of hydrogen (H$_2$) under a hydrogen pressure of from 20 to 45 bar (absolute).

5. The method according to claim 1, wherein the hydrodeoxygenation (HDO) reaction is carried out at a temperature of at least 280° C.

6. The method according to claim 5, which further comprises:
   a separation step of removing at least unreacted levulinic acid before the HDO reaction.

7. The method according to claim 1, which comprises:
   a separation step of removing at least unreacted levulinic acid before the HDO reaction.

8. The method according to claim 1, wherein the C—C coupling reaction is carried out in a presence of hydrogen ($H_2$) under a hydrogen pressure of 20 bar (absolute) or more.

9. The method according to claim 1, wherein the C—C coupling reaction in the conversion step is carried out in the presence of hydrogen under a hydrogen pressure of less than 25 bar (absolute).

10. The method according to claim 9, wherein the mild HDO step employs a hydrogenation catalyst and wherein the hydrogenation catalyst is a NiMo catalyst or a metal catalyst.

11. The method according to claim 1, wherein the C—C coupling reaction in the conversion step is carried out in the presence of hydrogen under a hydrogen pressure in the range of 1-20 bar (absolute).

12. The method according to claim 1, wherein the mild HDO step employs a hydrogenation catalyst and wherein the hydrogenation catalyst is a NiMo catalyst or a metal catalyst.

13. The method according to claim 12, wherein the hydrogenating metal carried by the acidic ion exchange resin is selected from metals of Group VIII of the Periodic Table of Elements.

14. The method according to claim 1, wherein the hydrogenating metal carried by the acidic ion exchange resin is selected from metals of Group VIII of the Periodic Table of Elements.

15. The method according to claim 1, wherein the C—C-coupling reaction is conducted at a temperature in the range of 100-200° C.

16. The method according to claim 15, wherein the C—C-coupling reaction is conducted at a temperature in the range of 120-140° C.

17. A method for conversion of levulinic acid comprising:
providing a feedstock containing at least levulinic acid; and
a conversion step of subjecting the feedstock to a C—C coupling reaction, wherein the C—C coupling reaction is carried out using an acidic ion exchange resin carrying a hydrogenating metal as a catalyst and under a hydrogen pressure of 3 bar (absolute) or less, and to a hydrotreatment so as to produce a product containing levulinic acid dimer derivatives having 4 oxygen atoms, wherein the hydrotreatment is carried out in a separate mild hydrodeoxygenation (HDO) step after the C—C coupling reaction at a temperature of from 235° C. to 270° C. so as to produce the product containing levulinic acid dimer derivatives having 4 oxygen atoms;
adjustment of levulinic acid dimer derivatives having 4 oxygen atoms by performing a mild hydrogenation step after completion of the C—C coupling reaction and the mild HDO step; and
wherein the method includes a hydrodeoxygenation step of subjecting at least the levulinic acid dimer derivatives to a hydrodeoxygenation (HDO) reaction to produce a HDO product, wherein a content of levulinic acid dimer derivatives having 4 oxygen atoms relative to all levulinic acid dimer derivatives subjected to the HDO reaction is 20 wt.-% or more, and wherein the HDO product contains at least 5% by weight of hydrocarbons derived from levulinic acid trimers.

18. A method for conversion of levulinic acid comprising:
providing a feedstock containing at least levulinic acid; and
a conversion step of subjecting the feedstock to a C—C coupling reaction, wherein the C—C coupling reaction is carried out using an acidic ion exchange resin carrying a hydrogenating metal as a catalyst and under a hydrogen pressure of 40 bar (absolute) or more, and to a hydrotreatment so as to produce a product containing levulinic acid dimer derivatives having 4 oxygen atoms, wherein the hydrotreatment is carried out in a separate mild hydrodeoxygenation (HDO) step after the C—C coupling reaction at a temperature of from 235° C. to 270° C. so as to produce the product containing levulinic acid dimer derivatives having 4 oxygen atoms;
adjustment of levulinic acid dimer derivatives having 4 oxygen atoms by performing a mild hydrogenation step after completion of the C—C coupling reaction and the mild HDO step; and
wherein the method includes a hydrodeoxygenation step of subjecting at least the levulinic acid dimer derivatives to a hydrodeoxygenation (HDO) reaction to produce a HDO product, wherein a content of levulinic acid dimer derivatives having 4 oxygen atoms relative to all levulinic acid dimer derivatives subjected to the HDO reaction is 20 wt.-% or more, and wherein the HDO product contains at least 5% by weight of hydrocarbons derived from levulinic acid trimers.

19. The method according to claim 1, wherein the content of levulinic acid dimer derivatives having 4 oxygen atoms and no carbon-carbon double bonds is 30 wt.-% or more based on the total amount of levulinic acid dimer derivatives having 4 oxygen atoms and/or the total content of levulinic acid dimer derivatives having 4 oxygen atoms and no carbon-carbon double bonds and levulinic acid dimer derivatives having 4 oxygen atoms and at least one carbon-carbon double bonds is 40 wt.-% or more based on the total amount of levulinic acid dimer derivatives having 4 oxygen atoms.

* * * * *